(12) United States Patent
Spivey (10) Patent No.: US 9,585,557 B1
(45) Date of Patent: Mar. 7, 2017

(54) SPECTRAL FLYING SPOT EYE-TRACKER AND HEADS-UP DISPLAY (71) Applicant: Alvin Spivey, Fairfax, VA (US)

(72) Inventor: Alvin Spivey, Fairfax, VA (US)

( * ) Notice: Subject to any disclaimer, the term of this patent is extended or adjusted under 35 U.S.C. 154(b) by 0 days.

(21) Appl. No.: 14/505,502

(22) Filed: Oct. 3, 2014

Related U.S. Application Data (60) Provisional application No. 61/886,431, filed on Oct. 3, 2013.

(51) Int. Cl.
*A61B 3/14* (2006.01)
*A61B 3/113* (2006.01)
*G02B 27/01* (2006.01)

(52) U.S. Cl.
CPC ............ *A61B 3/113* (2013.01); *G02B 27/017* (2013.01); *G02B 2027/0178* (2013.01)

(58) Field of Classification Search
CPC .................................. A61B 3/113; A61B 3/14
USPC .................................................. 351/200–247
See application file for complete search history.

(56) References Cited

U.S. PATENT DOCUMENTS

| 6,120,461 | A  | 9/2000  | Smyth            |
|-----------|----|---------|------------------|
| 6,227,667 | B1 | 5/2001  | Halldorsson et al. |
| 6,299,308 | B1 | 10/2001 | Voronka et al.   |
| 7,712,901 | B2 | 5/2010  | Wernick et al.   |
| 8,048,065 | B2 | 11/2011 | Grecu et al.     |
| 8,113,657 | B2 | 2/2012  | Eberl et al.     |
| 8,235,529 | B1 | 8/2012  | Raffle et al.    |
| 8,911,090 | B2 * | 12/2014 | Furman ............. A61B 3/113 351/158 |
| 2010/0134761 | A1 * | 6/2010 | Johns ............... A61B 5/18 351/209 |
| 2014/0232989 | A1 * | 8/2014 | Gramatikov ....... A61B 3/0091 351/211 |
| 2015/0223678 | A1 * | 8/2015 | Goldfain ........... A61B 1/227 600/200 |

FOREIGN PATENT DOCUMENTS

WO  2009126264 A2  10/2009

OTHER PUBLICATIONS http://www.gizmag.com/jins-meme-smart-glasses-energy-levels/35317/.
Jins Meme, https://www.jins-jp.com/jinsmeme/en/.

* cited by examiner

*Primary Examiner* — Mahidere Sahle
(74) *Attorney, Agent, or Firm* — Quickpatents, LLC; Kevin Prince (57) ABSTRACT A tracking and display system for an eye of a person is incorporated into eyewear having at least one lens and being positionable in front of the eye or eyes with attachment hardware. A circuit with a power source is fixed with the eyewear and includes at least one multispectral LED adapted to project light towards the eye and at least one multispectral light detector adapted to receive light reflected from the eye. As such, movement, anatomy and physiology of the eye are determined according to an organized pattern of projected light reflected and received by the at least one detector. To display an image, light from the at least one multispectral LED is conveyed by at least one optical fiber to an eye-facing surface of a lens of the eyewear and then onto the retina of the person's eye to form a visible heads-up display image.

19 Claims, 8 Drawing Sheets

SPECTRAL FLYING SPOT EYE-TRACKER AND HEADS-UP DISPLAY

CROSS-REFERENCE TO RELATED APPLICATIONS

This application claims the benefit of U.S. Provisional Patent Application 61/886,431, filed on Oct. 3, 2013, and incorporated herein by reference.

STATEMENT REGARDING FEDERALLY SPONSORED RESEARCH AND DEVELOPMENT

Not Applicable.

FIELD OF THE INVENTION

This invention relates to eye tracking diagnostic devices and heads-up display, and more particularly to a tracking, sensing, and display system incorporated into eyewear.

DISCUSSION OF RELATED ART

Miniature wearable spectrometer devices are replete within eye-tracking technologies. Usually including a monochromatic infrared sensor, these miniature devices tend to be placed along the side of eyewear, are composed of intricately designed proximal optics like the device taught in U.S. Pat. No. 8,113,657 to Eberl et al. on Feb. 14, 2012, and are in some sense dynamic. Representative of the most advanced forms, U.S. Pat. No. 7,712,901 to Wernick et al. on Dec. 6, 2007 exploits the multispectral reflections of the eye measured by a camera.

To determine the optical axis and structural geometry of individual eyes, both U.S. Pat. No. 6,120,461 to Smyth et al. on Jun. 29, 2010 and U.S. Pat. No. 6,227,667 to Halldorsson et al. on May 8, 2001 modulate incident laser illumination, then employ an algorithm to reorganize the modulated light into anatomical descriptions. These algorithms exploit what the eye-tracking devices sense (i.e. gaze tracking algorithms, retinal maps, or measurements of binocular disparity), to reconstruct eye geometries. See also U.S. Pat. No. 8,235,529 to Raffle et al. on Nov. 20, 2011, for example.

In the simplest forms of eye-tracking hardware, U.S. Pat. No. 8,048,065 to Crecu et al. on Dec. 23, 2002 and U.S. Pat. No. 6,299,308 to Voronka et al. on Oct. 9, 2001 diffusely illuminate an eye and detect the immediate reflection off of the eye. No modulation of the source illumination, or optical system to redirect irradiance, are used in these straightforward designs.

If not used as a tool for ophthalmic surgery, eye-tracking device technology is aligned with a display, particularly a heads-up display (HUD). International Patent application WO 2009/126264 to Chaum et al. on Apr. 6, 2009 teaches a device that raster scans a laser onto the retina to create an image, projecting images in front of the eye from reflected surfaces, spatially exploiting the vision field of view.

Therefore, there is a need for a device that diffusely illuminates the eye through a lens to structure the multispectral illumination profile into a pattern that best maps eye reflection and eye position. Such a needed eye tracker would not modulate incident light, nor make any assumption about eye anatomy other than that the eye anatomy is composed of ellipsoidal surfaces. Such a simple design and loose assumptions about the eye would allow the needed eye-tracker to be mobile while exploiting precise measurement of individual eye-position.

SUMMARY OF THE INVENTION

The present device is a tracking and display system for sensing movement, anatomy and physiology of an eye of a person. The tracking and display system is incorporated into eyewear having at least one lens and being positionable in front of the eye or eyes with attachment hardware. Preferably the eyewear is a pair of eyeglasses having two of the lenses, and wherein the attachment hardware includes a frame pivotally attached at opposing sides thereof to two temple pieces at a hinge.

A circuit comprises at least a microprocessor, an accelerometer, a gyrometer, a transceiver, and a power source, all fixed within a top side of the frame and temple pieces. At least one multispectral LED is fixed with or within the eyewear and is adapted to project light towards the eye. At least one multispectral light detector is fixed with or within the eyewear and is adapted to receive light reflected from the eye. In one embodiment, the at least one multispectral light detector is two multispectral light detectors each fixed adjacent one of the lenses proximate to a nose portion of the eyeglasses. Further, the at least one multispectral LED is two multispectral LEDs each fixed adjacent one of the lenses proximate to the nose of the eyeglasses.

In one embodiment, each detector and LED is fixed proximate one of the temple pieces. In such an embodiment, the system further includes a cooperative medium, such as at least one fiber optic strand, fixed between each detector and LED of each temple piece and one of the lenses and preferably fixed at least partially surrounding one of the lenses. The cooperative medium is adapted to convey light therethrough. As such each detector and LED can be fixed to a rear end of one or both temple pieces to reduce weight of the eyeglasses on the person's nose. In one embodiment, the cooperative medium is adapted to convey light from the at least one multispectral LED to the surface of the person's nose, whereby movement of the eyeglasses relative to the person's nose may be detected by the at least one multispectral light detector.

In one embodiment, each cooperative medium surrounding one of the lenses projects a patterned illumination profile across the eye. Further, each lens preferably is layered and diffusely scatters light onto the surface of the eye. Such layers on each lens may include a scratch resistant film A, a flash color coating B for mirrored lenses, a UVA/UVB filter, an IR scatterer D, and a polarized polycarbonate core E. In such an embodiment, the IR scatterer D may be of the type that has a reflective pattern that reflects IR wavelengths in the patterned illumination profile across the eye. As such, movement, anatomy and physiology of the eye are determined according to an organized pattern of projected light reflected and received by the at least one detector.

To display an image to the person, light from the at least one multispectral LED is conveyed by the at least one cooperative medium to an eye-facing surface of each lens and then onto the retina of the person's eye. Such light entering the person's eye forms a visible heads-up display image.

The present invention is a device that diffusely illuminates the eye through a lens to structure the multispectral illumination profile into a pattern that best maps eye reflection and eye position. The present eye tracking device does not modulate incident light, nor relies on any assumption about eye anatomy other than that the eye anatomy is composed of ellipsoidal surfaces. Such a simple design and loose assumptions about the eye allows the present eye-tracker to be mobile while exploiting precise measurement of individual eye-position. Other features and advantages of the present invention will become apparent from the following more detailed description, taken in conjunction with the accompanying drawings, which illustrate, by way of example, the principles of the invention.

DETAILED DESCRIPTION OF THE PREFERRED EMBODIMENT

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list. When the word "each" is used to refer to an element that was previously introduced as being at least one in number, the word "each" does not necessarily imply a plurality of the elements, but can also mean a singular element.

TERMINOLOGY AND LEXICOGRAPHY

Eye-tracker: A device that is used to sense the movement and anatomy of an eye.

Heads-Up Display (HUD): A virtual scene created by quickly imaging across the focal plane of an eye.

Cooperative Medium: Any material or structure that is amenable to the transport of relevant electromagnetic energy. Amenability is with regard to indices of refraction and quantum efficiency.

Layered lens: Example layers include, but are not limited to, a scratch resistant film 42A, a 100% UVA/UVB 400 filter 42C, an IR reflector 42D, a polarized polycarbonate core 42E, and a flash color coating 42B.

Visual System: The whisking eye movement, light detection, and further brain processing of electromagnetic energy received by the eye's optics.

Pixel: The least spatially resolvable point of brightness and/or color sequentially projected into the eye by the invention.

FIGS. 1-4 illustrate a tracking and display system 10 for sensing movement, anatomy and physiology of an eye 22 of a person 20.

Figure 2:
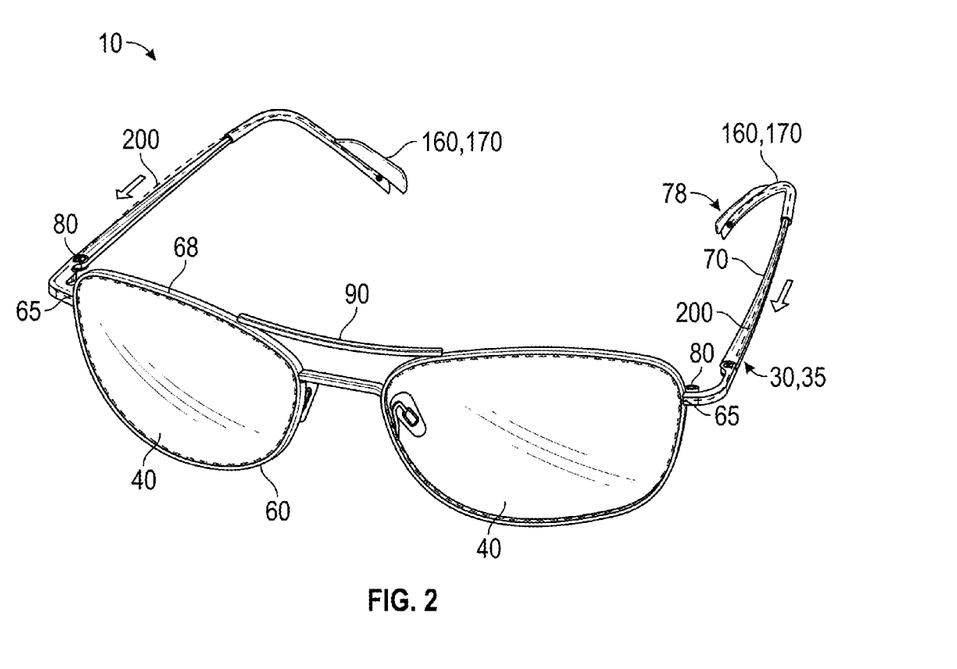
FIG. 2 is a perspective view of the invention as incorporated into a pair of eyeglasses, illustrating light paths from an LED source to a pair of lenses.
Figure 3:
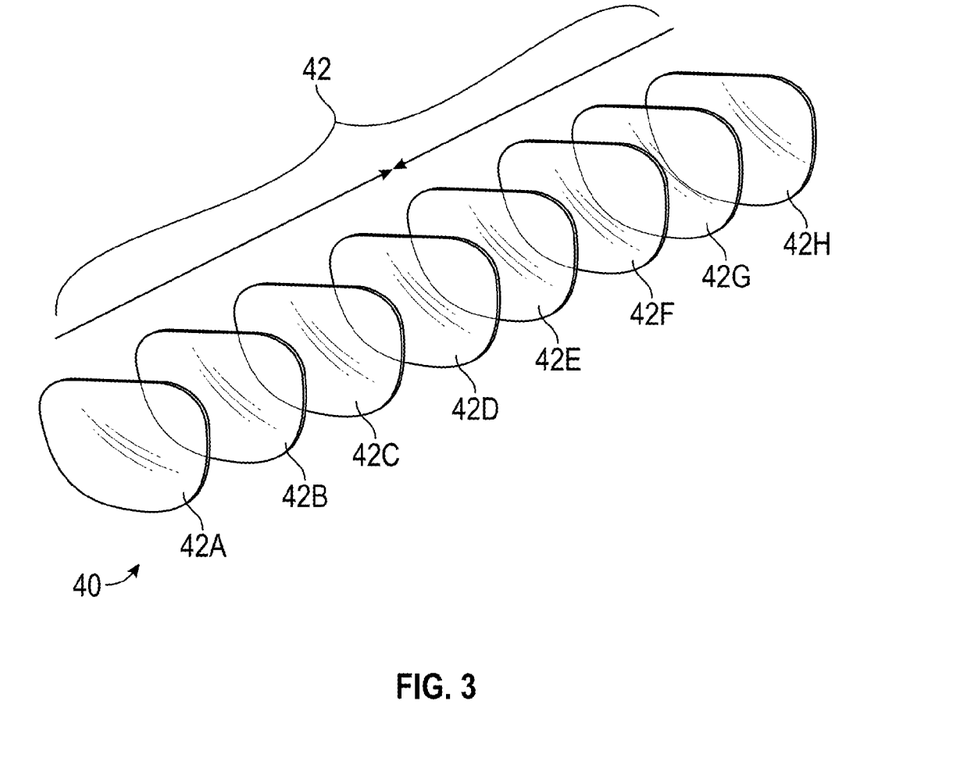
FIG. 3 is an exploded view of one embodiment of an eyeglass lens of the invention.
Figure 4:
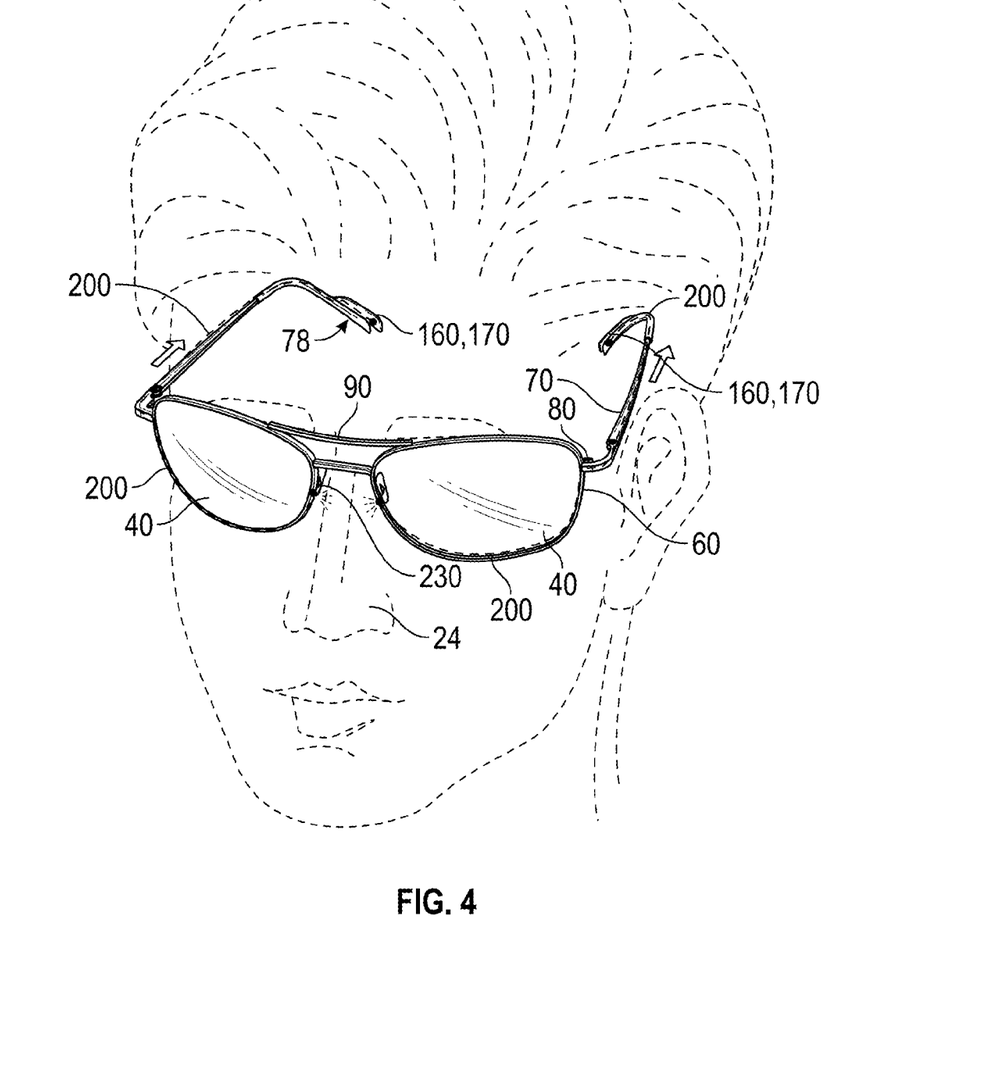
FIG. 4 is a perspective view of the embodiment of FIG. 2, illustrating light paths from the lenses to a light detector.

The tracking and display system 10 is incorporated into eyewear 30 having at least one lens 40 and being positionable in front of the eye 22 or eyes 22 with attachment hardware 50. Preferably the eyewear 30 is a pair of eyeglasses 35 having two of the lenses 40, and wherein the attachment hardware 50 includes a frame 60 pivotally attached at opposing sides 65 thereof to two temple pieces 70 at a hinge 80 (FIGS. 2-4).

A circuit 100 (FIG. 1) comprises at least a microprocessor 110, an accelerometer 120, a gyrometer 130, a transceiver 140, and a power source 150, all fixed with a top side 68 of the frame 60 and temple pieces 70.

At least one multispectral LED 160 is fixed the eyewear 30 and is adapted to project light 165 towards the eye 22. At least one multispectral light detector 170 is fixed with the eyewear 30 and is adapted to receive light reflected from the eye 22. In one embodiment, the at least one multispectral light detector 170 is two multispectral light detectors 170 each fixed adjacent one of the lenses 40 proximate to a nose 90 portion of the eyeglasses 35. Further, the at least one multispectral LED 160 is two multispectral LEDs 160 each fixed adjacent one of the lenses 40 proximate to the nose 90 of the eyeglasses 35.

In one embodiment, each detector 170 and LED 160 is fixed proximate one of the temple pieces 70. In such an embodiment, the system 10 further includes a cooperative medium 200, such as at least one fiber optic strand, fixed between each detector 170 and LED 160 of each temple piece 170 and one of the lenses 40 and preferably fixed at least partially surrounding one of the lenses 40. The cooperative medium 200 is adapted to convey light therethrough. As such each detector 170 and LED 160 can be fixed to a rear end 78 of one or both temple pieces 70 to reduce weight of the eyeglasses 35 on the person's nose. In one embodiment, the cooperative medium 200 is adapted to convey light from the at least one multispectral LED 160 to the surface of the person's nose 24, whereby movement of the eyeglasses 35 relative to the person's nose 24 may be detected by the at least one multispectral light detector 170.

In one embodiment, each cooperative medium 200 surrounding one of the lenses 40 projects a patterned illumination 210 profile across the eye 22. Further, each lens 40 preferably is layered and diffusely scatters light onto the surface of the eye 22 (FIG. 3). Such layers on each lens 40 may include a scratch resistant film 42A, a flash color coating 42B for mirrored lenses 40, a UVA/UVB 400 filter 426, an IR scatterer 42D, and a polarized polycarbonate core 42E. In such an embodiment, the IR scatterer 42D may be of the type that has a reflective pattern 220 that reflects IR wavelengths in the patterned illumination profile 210 across the eye 22.

As such, movement, anatomy and physiology of the eye 22 are determined according to an organized pattern of projected light reflected and received by the at least one detector 170.

Figure 6:
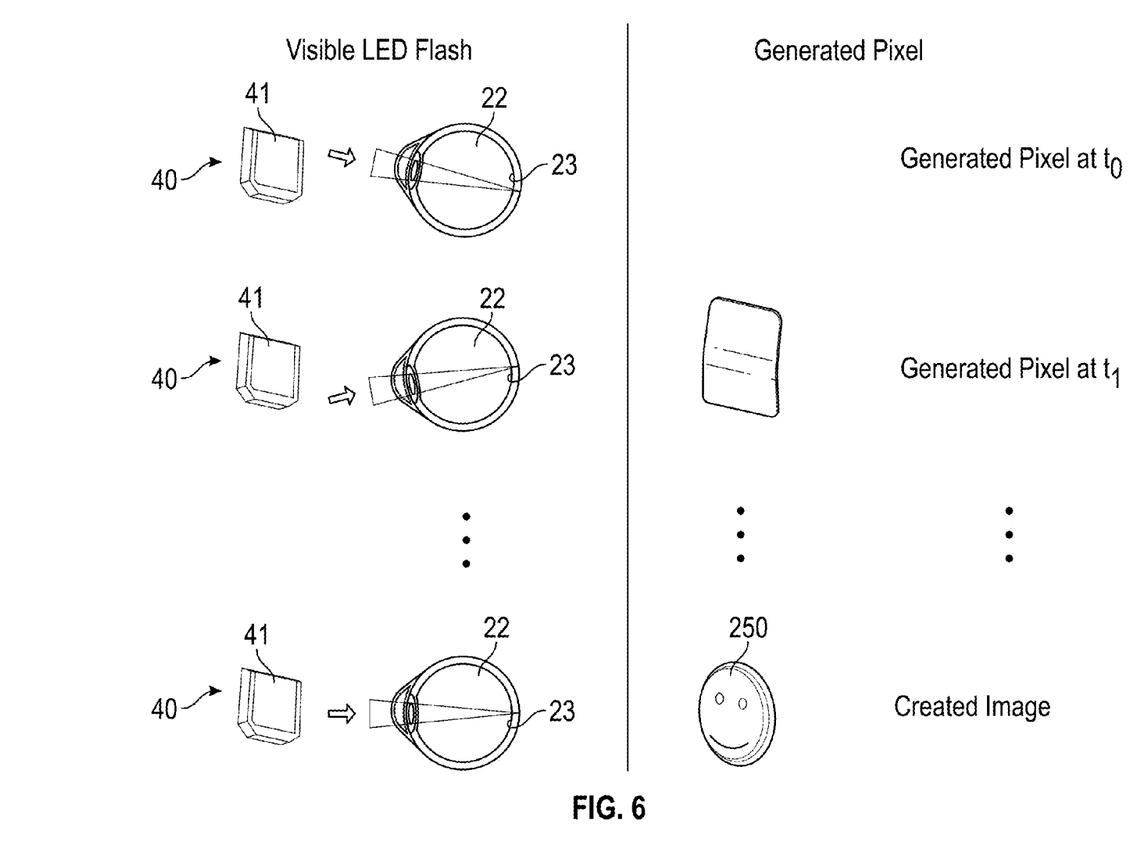
FIG. 6 is a diagram showing how an image is incrementally formed on a person's retina based on eye position.
Figure 7:
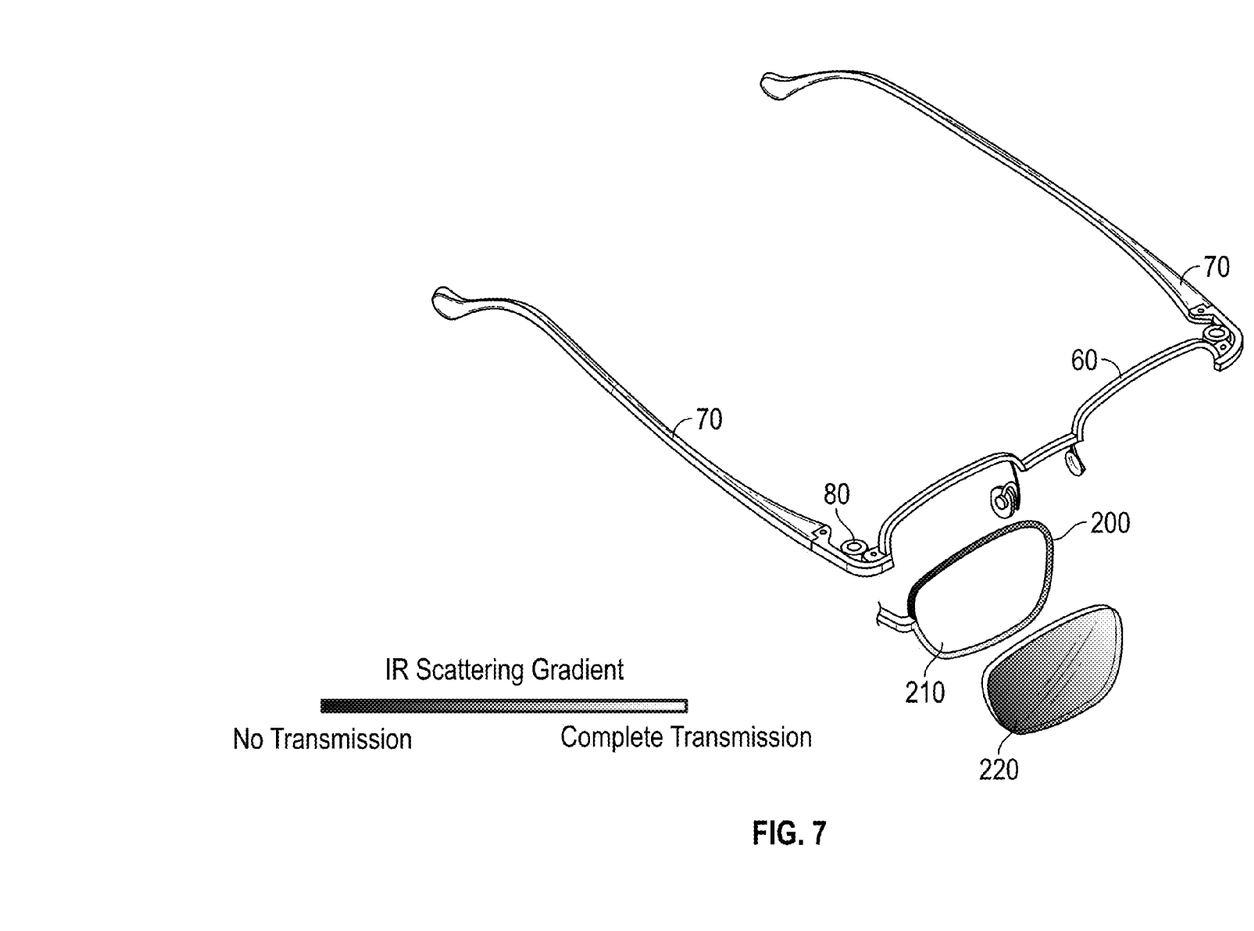
FIG. 7 is a diagram showing a reflective pattern that reflects IR wavelengths in a patterned illumination profile of a lens.

To display an image to the person 20, light from the at least one multispectral LED 160 is conveyed by the at least one cooperative medium 200 to an eye-facing surface 41 of each lens 40 and then onto the retina 23 of the person's eye 22 (FIG. 6). Such light entering the person's eye 22 forms a visible heads-up display image 250.

The system 10 may further include batteries 10, operational amplifiers 13, and a logical sequence of pixels 80.

Figure 1:
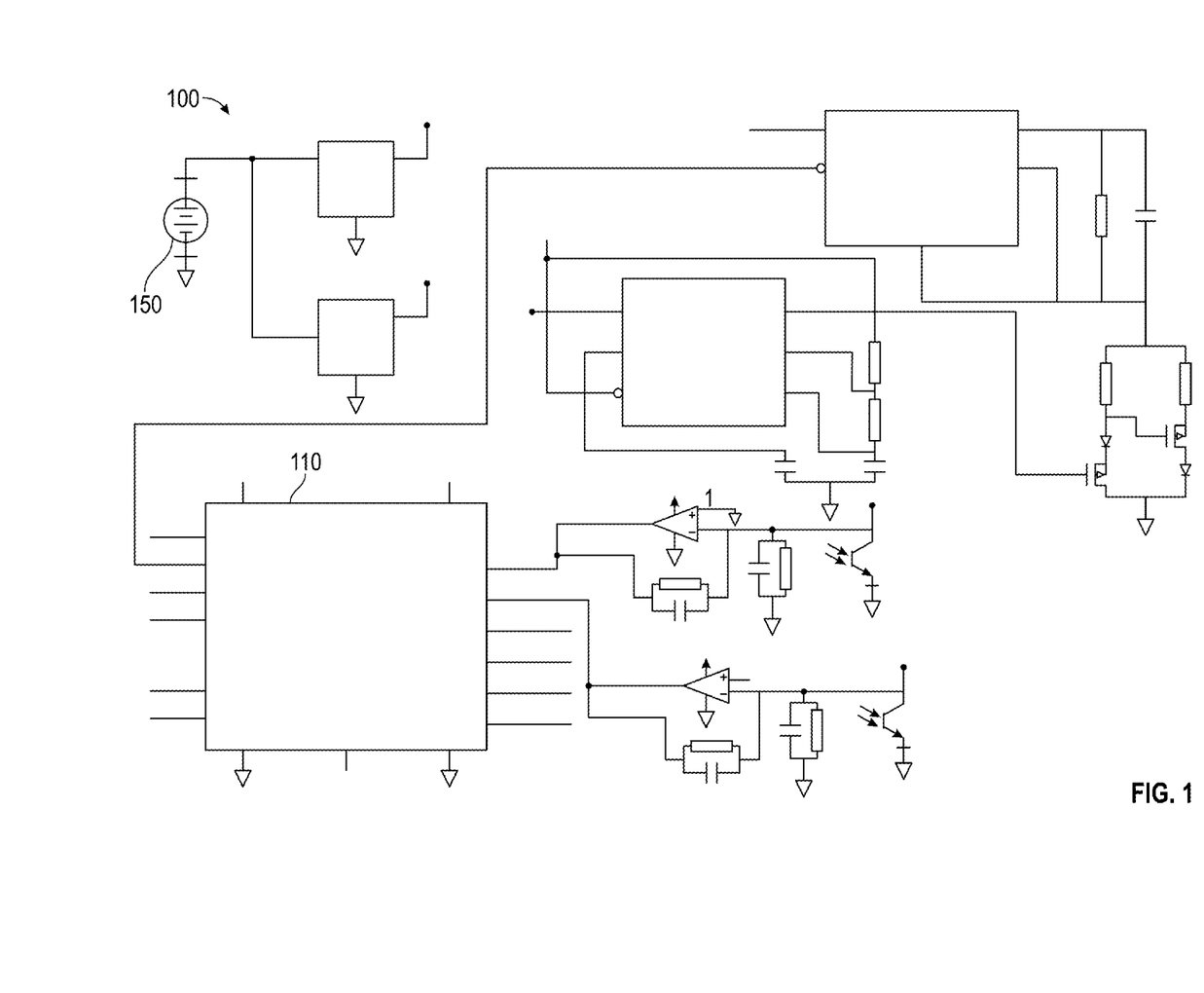
FIG. 1 is an electrical schematic of one embodiment of the invention.

In reference to FIG. 1, an example of the eye-tracker circuit 100 is shown powered by at least one battery 102 powering the multiple wavelength LEDs 160 and a multiple wavelength light detector 170 connected to operational amplifiers 203 to amplify and stabilize a voltage output. The output voltages from the multiple wavelength detector 170, transmits externally via the transceiver 140. The circuit 100 also powers the accelerometer 120, gyrometer 130, microprocessor 110, and an additional multiple wavelength LED 160 and multiple wavelength detector 170 pair.

In reference to FIG. 2, electromagnetic energy is transported from the multiple wavelength LED 160 within a rear end 78 the temple piece 70, along the temple 70, through an eyewear hinge 80, and along the eyewear frame 60. The lens 40 area along the frame 60 has a gradient of electrometric energy transmittance that passes electromagnetic energy through that area of the lens 40, into the lens 40. From within the lens 40, the transported electromagnetic energy is scattered by the layered polarized polycarbonate lens 40, onto the corneal surface of the eye 22.

In reference to FIG. 4, electromagnetic energy reflects off of the corneal surface of the eye 22 and into the cooperative medium 200 that is fixed along the frame 60, through the hinge 80 and temple 70, and into the rear end 78 of the temple 70 where the set of multiple wavelength detectors 170 detect the reflected electromagnetic energy.

Figure 5A:
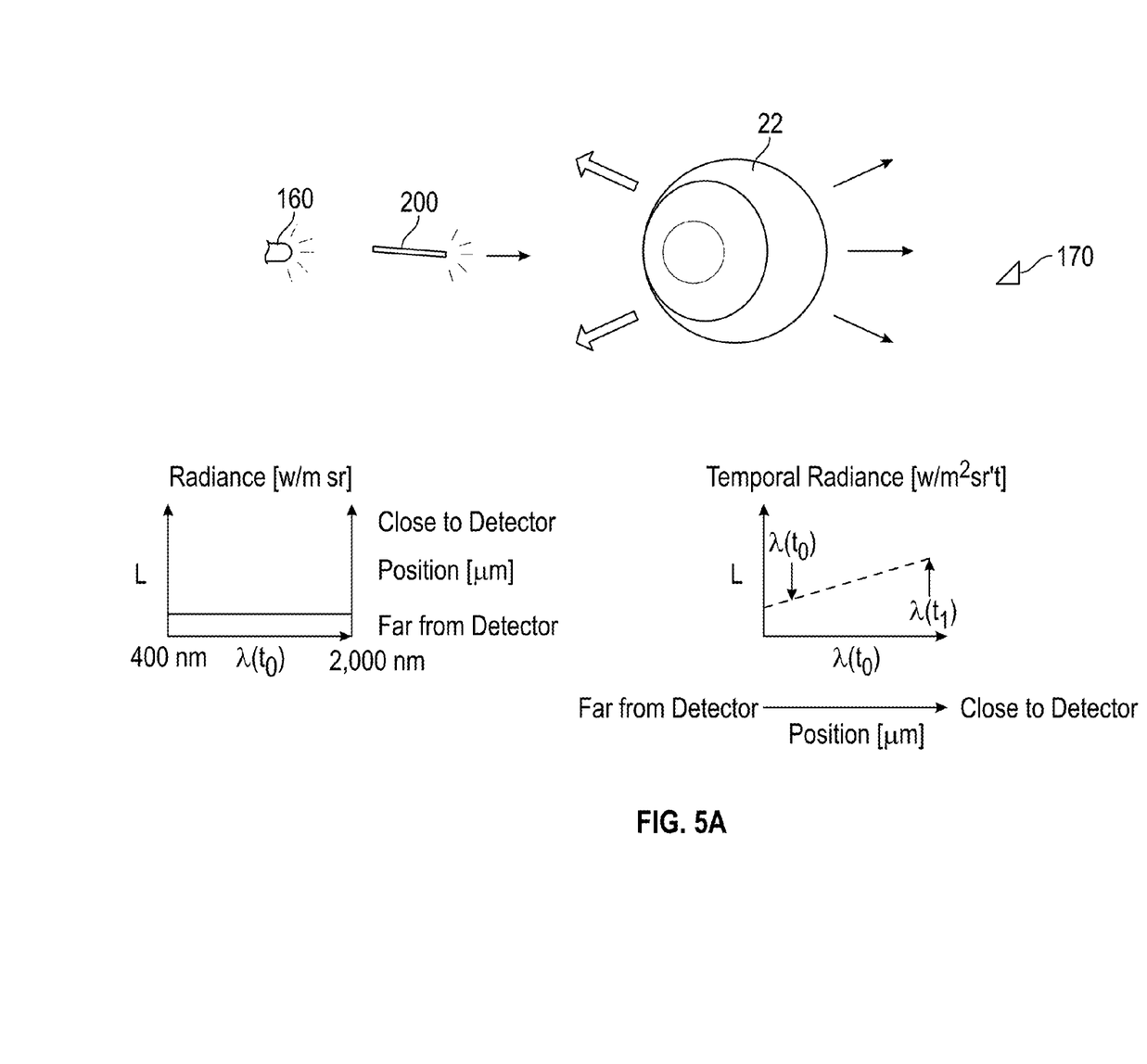
FIG. 5A is a diagram of a person's eye in a first position and a resultant radiance curve.
Figure 5B:
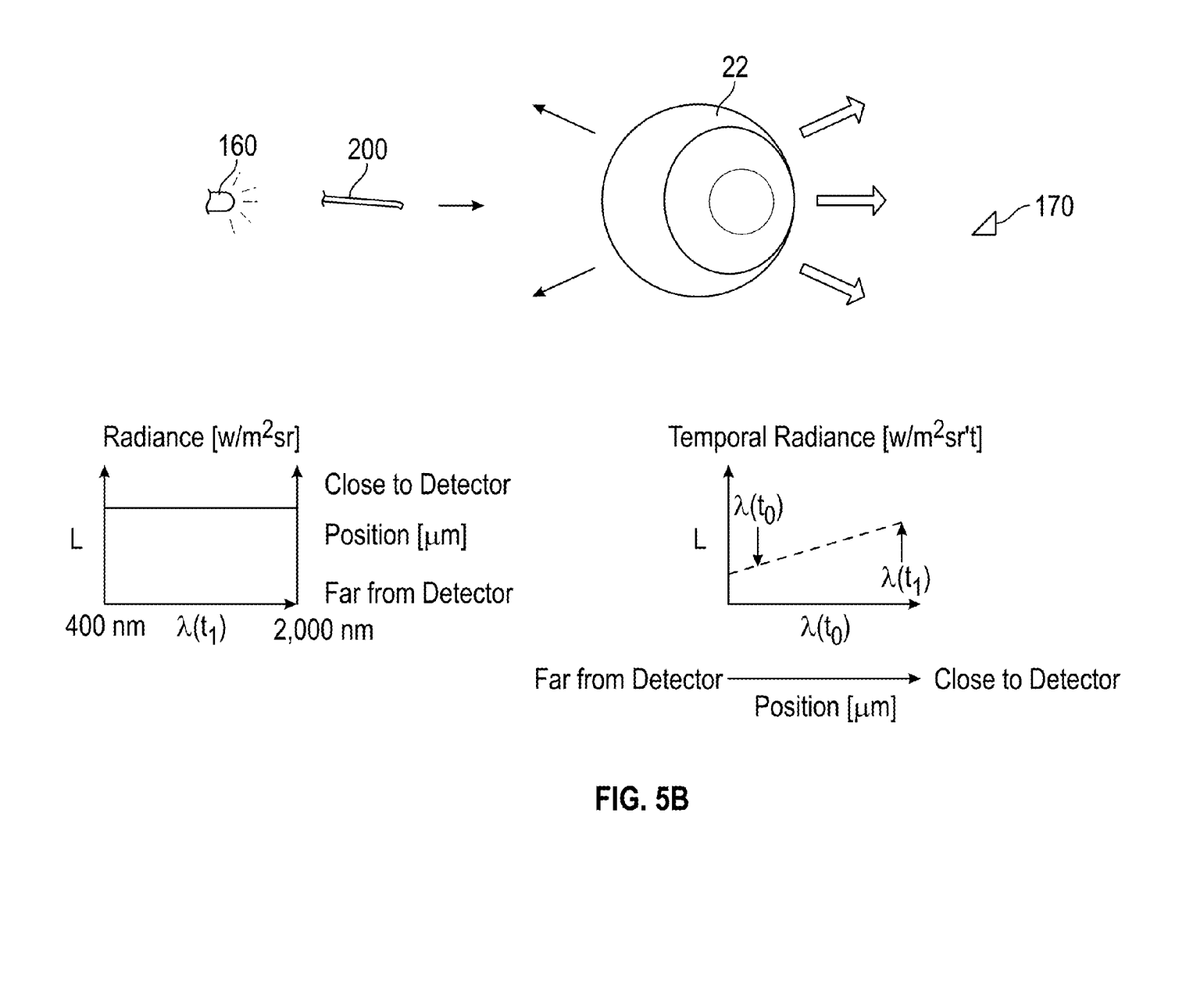
FIG. 5B is a diagram of the eye in FIG. 5A in an alternate position and a resultant radiance curve.

In reference to FIG. 5, the gradient of electromagnetic energy transmittance that passes electromagnetic energy through the area of the layered lens 26 from the eye wire/rim 23, and into the layered lens 26, is such that the reflectance intensity measured off of the corneal surface is unique for every orientation that the corneal surface can have. Thus, precise measurement of the reflectance intensity from the corneal surface is a precise measurement of the orientation of the eye. Additionally, this measurement of the corneal surface can similarly be done for any ocular surface of the eye—including but not limited to the sclera, front surface of the eye lens, back surface of the eye lens, and internal structure of the eye. Having determined each of the component structure, location, and orientation eye spectroscopy can be practiced.

To compensate for any change in the relationship between ocular surface reflected brightness and eye orientation due to movement of the eyewear 30, movement of the eyewear 30 at the nose 24 along the skin is measured. This measurement is made by detecting the electromagnetic energy that is transported from the multiple wavelength LED 160 through to the skin-facing side proximate the nose portion 90. The electromagnetic energy reflected off of the skin, from under the skin-facing side of the nose 90, is transported through the cooperative medium 200 and into the multiple wavelength detector 170. The direction and magnitude of eyewear movement across the surface of the skin may be detected by having a plurality of the cooperative medium 200 isolated from each other and organized at a fixed distance apart proximate the person's skin.

In reference to FIG. 6, to create the heads-up display, a virtual scene or image 250 is generated by taking advantage of limitations in the human visual system. Given an orientation for the eye 22, the back of the lens 40 may be illuminated with visible intensity. Corresponding to the brain's ability to process visible electromagnetic intensity, the hue, saturation, and brightness is changed to produce a single pixel 255. Accordingly, for every orientation of the eye a pixel 255 is sequentially mapped. This sequential pixel 255 generation for every eye orientation creates the virtual image 250 and defines the heads-up display visualization.

While a particular form of the invention has been illustrated and described, it will be apparent that various modifications can be made without departing from the spirit and scope of the invention. For example, the system may be incorporated into a face shield (not shown), visor (not shown), or other head-worn implement. Accordingly, it is not intended that the invention be limited, except as by the appended claims.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. A tracking and display system for sensing movement, anatomy and physiology of an eye of a person, comprising:
   eyewear having at least one lens and positionable in front of the eye with attachment hardware, wherein the eyewear is a pair of eyeglasses having a front frame and two temple pieces extending from the front frame;
   at least one multispectral LED fixed with the one of the temple pieces of the eyewear and adapted to project light towards the eye;
   a cooperative medium between the at least one multispectral LED and the at least one lens, the cooperative medium conveying light from the LED to the lens;
   at least one multispectral light detector fixed with the eyewear and adapted to receive light reflected from the eye;
   whereby movement, anatomy and physiology of the eye are determined according to an organized pattern of project light reflected and received by the at least one detector.

2. The tracking and display system of claim 1 further including a circuit comprising at least a microprocessor, an accelerometer, a gyrometer, a transceiver, and a power source, all fixed with the eyewear.

3. The tracking and display system of claim 1 further including a circuit comprising at least a microprocessor, an accelerometer, a gyrometer, a transceiver, and a power source, all fixed with the eyewear.

4. The tracking a display system of claim 3 wherein the circuit is fixed with a top side of the frame and temple pieces.

5. The tracking display system of claim 1 wherein the at least one multispectral light detector is two multispectral light detectors.

6. The tracking display system of claim 1 wherein the at least one multispectral light detector is two multispectral light detectors each fixed with one of the temple pieces of the eyeglasses, and wherein the at least one multispectral LED is two multispectral LEDs each fixed with one of the temples of the eyeglasses, and wherein the cooperative medium is disposed between each detector/LED of each temple and one of the lenses to convey light therethrough.

7. The tracking display system of claim 6 wherein each cooperative medium is adapted to convey light between each temple and the frame at least partially surrounding one of the lenses.

8. The tracking display system of claim 7 wherein each cooperative medium surrounding one of the lenses projects a patterned illumination profile into the lens.

9. The tracking display system of claim 7 wherein the lens is layered and diffusely scatters light onto the surface of the eye.

10. The tracking display system of claim 7 wherein at least one of the layers of each lens has a transmissive pattern that scatters light in a patterned illumination profile across the eye.

11. The tracking display system of claim 7 wherein each cooperative medium includes at least one aperture for admitting light reflected from the eye for transmittal to the at least one multispectral light detector.

12. The tracking display system of claim 7 wherein each cooperative medium is adapted to convey light from the at least one multispectral LED to the surface of the person's nose.

13. The tracking display system of claim 12 wherein the at least one multispectral light detector detects light reflecting from the person's nose to detect movement of the eyewear with respect to the person's face.

14. The tracking display system of claim 6 wherein light from the at least one multispectral LED is conveyed by the at least one cooperative medium to an eye-facing surface of each lens and then onto the retina of the person's eye.

15. The tracking display system of claim 14 wherein the light enters into the person's eye according to eye position and plane of focus, forming a visible heads-up display image.

16. A tracking and display system for sensing movement, anatomy and physiology of an eye of a person, comprising:
   eyewear having at least one lens and positionable in front of the eye with attachment hardware, wherein the eyewear is a pair of eyeglasses having a front frame and two temple pieces extending from the front frame;
   at least one multispectral LED fixed with the eyewear and operable to provide light into the lens, where the lens diffusely scatters light onto the surface of the eye;
   at least one multispectral light detector fixed with the eyewear and adapted to receive light reflected from the eye;
   whereby movement, anatomy and physiology of the eye are determined according to an organized pattern of project light reflected and received by the at least one detector.

17. The tracking display system of claim 16 wherein the at least one multispectral light detector is two multispectral light detectors each fixed adjacent one of the lenses proximate to a nose portion of the eyeglasses, and the at least one multispectral LED is two multispectral LEDs each fixed adjacent one of the lenses proximate to the nose of the eyeglasses.

18. The tracking display system of claim 16 wherein the at least one multispectral light detector is two multispectral light detectors each fixed with one of the temple pieces of the eyeglasses, and wherein the at least one multispectral LED is two multispectral LEDs each fixed with one of the temples of the eyeglasses, and further including a cooperative medium is disposed between each detector/LED of each temple and one of the lenses, the cooperative medium adapted to convey light therethrough.

19. The tracking display system of claim 7 wherein each cooperative medium surrounding one of the lenses projects a patterned illumination profile into the lens.

* * * * *